United States Patent [19]

Herpichboehm et al.

[11] Patent Number: 4,871,258
[45] Date of Patent: Oct. 3, 1989

[54] COLOR TEST METER

[75] Inventors: Bernd G. Herpichboehm; George H. Sierra; Robert B. Summers; Thomas M. Watlington, all of Indianapolis, Ind.

[73] Assignee: Boehringer Mannheim Corporation, Indianapolis, Ind.

[21] Appl. No.: 187,857

[22] Filed: Apr. 29, 1988

[51] Int. Cl.⁴ ............................................. G01J 3/52
[52] U.S. Cl. ...................................... 356/422; 356/42; 356/423; 364/413.09
[58] Field of Search ........................... 356/42, 421–425; 434/98, 101; 364/413.09, 413.11, 526

[56] References Cited

U.S. PATENT DOCUMENTS

| 2,523,758 | 9/1950 | Gould | 356/42 |
| 4,461,829 | 7/1984 | Greenquist | 435/7 |
| 4,509,859 | 4/1985 | Markart et al. | 356/446 |
| 4,523,852 | 6/1985 | Bauer | 356/421 |

FOREIGN PATENT DOCUMENTS

| 0100619 | 2/1984 | European Pat. Off. | |
| 0110173 | 6/1984 | European Pat. Off. | |
| 0207360 | 1/1987 | European Pat. Off. | |
| 224666 | 7/1985 | Fed. Rep. of Germany | 356/425 |

Primary Examiner—F. L. Evans
Attorney, Agent, or Firm—Barnes & Thornburg

[57] ABSTRACT

A colorimeter comprises a case, a liquid crystal display (LCD) mounted on the case, a color chart provided on the case to permit holding of a specimen to be compared in close proximity to the color chart, and switches for indicating which color on the color chart the color of the specimen most closely approximates. Each switch is located adjacent a color on the color chart, and the states of the switches drive the LCD to display a reading corresponding to the color on the color chart which most closely approximates the color of the specimen.

3 Claims, 5 Drawing Sheets

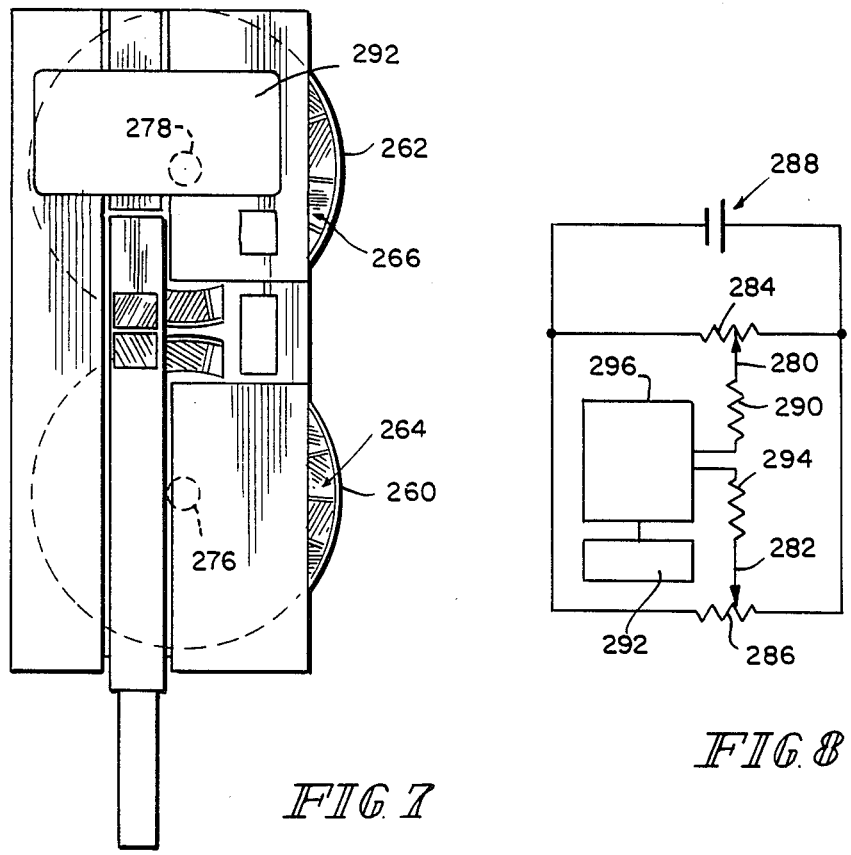
FIG. 7
FIG. 8
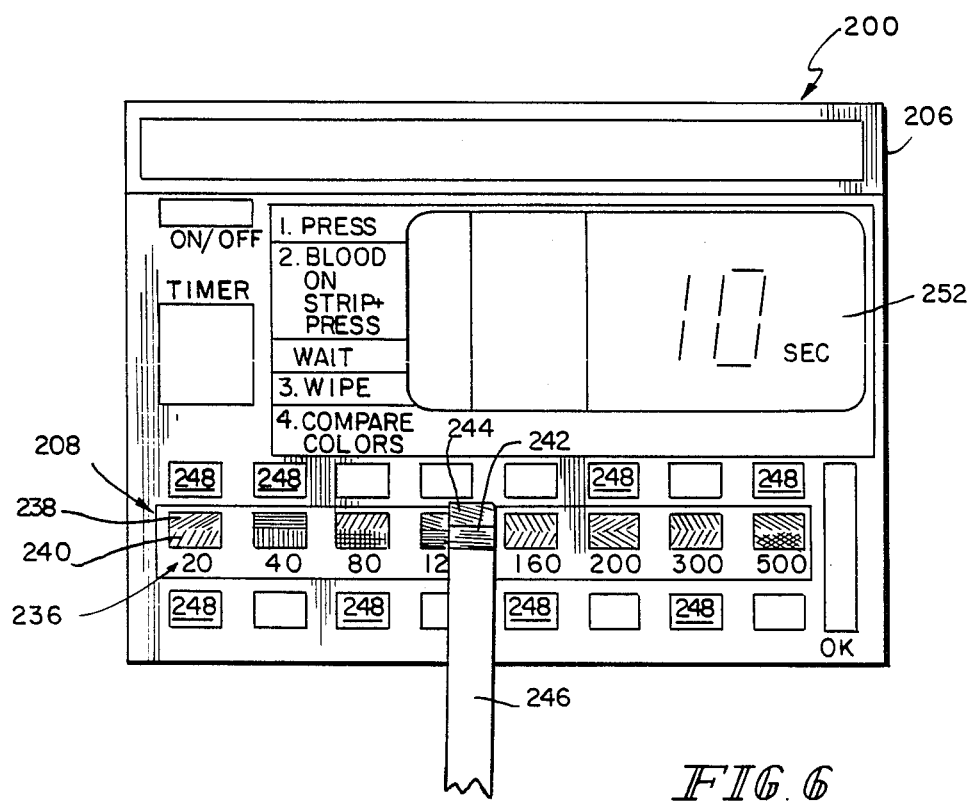
FIG. 6

COLOR TEST METER

This invention relates to colorimeters. It is disclosed in the context of an apparatus for measuring the concentration of a medically significant component of a biological fluid. However, it is believed that the invention would be useful in other applications as well.

Dry chemistries for determining concentrations of medically significant constituents of, for example, biological fluids have been in use for years. An example would be the chemical strips to which chemistries are affixed and tapes impregnated with chemistries, which chemistries react with, for example glucose in blood or urine to provide indications of blood glucose for use in regulating the administration of insulin in diabetics. The chemistries on or in these chemical strips and tapes react with the medically significant component of the body fluid into contact with which they are brought. Reactions involving the medically significant component and the chemistry induce color changes in the chemistry itself or some other associated component of the strip or test tape. The color of the chemistry or associated component after some predetermined reaction time can be compared to standards prepared by suitable means to give an indication of the concentration of the medically significant component in the body fluid.

Typically, the standards are reproduced on a chart mounted on the outside of a vial or other container for the strips or tapes. The colors on the charts are indicative of specific concentrations which are printed with the colors. Sometimes it is hard, owing to the nature of the charts, their design, their mounting on the container, and other factors, to obtain a positive, accurate comparison of the strip's or tape's color to a color printed on the chart.

Often, the reacted color of the strip or tape will lie between two colors which are not adjacent each other on the chart. It is hard to put the strip or tape close enough to both to ascertain positively that the reacted color does indeed lie between them. This makes reading the strip or tape more difficult. Of course, the easier it can be made to obtain an accurate reading of the concentration of the medically significant component in the body fluid, the more reliable and valuable the particular combination of strip or tape and chart becomes.

Certain equipment has been designed to read the reacted colors from strips and convert the color readings into displays of corresponding concentration of the medically significant component in the biological fluid. In many cases, this equipment is quite expensive. As a result, some users, for example, diabetics who need to test their blood glucose levels regularly, can't afford an expensive piece of equipment to interpret results. They continue to rely on visual matching of the chart and strip colors and conversion of those into glucose concentrations.

The following listed references provide some background regarding the various chemistry systems, substrates or carriers, and reaction-reading equipment known to those skilled in the art to which the invention pertains: U.S. Pat. No. 4,461,829 and references cited there; U.S. Pat. No. 4,509,859 and references cited there; European patent application No. 0100619A1 and references cited there; European patent specification 0110173B1 and references cited there; and European patent application No. 0207360A2 and references cited there. No representation is made hereby that this list is exhaustive or that more Pertinent Prior art is not available.

It is a primary object of the present invention to provide an inexpensive apparatus for timing the reaction interval(s), comparing the reacted color(s) to the color charts, and providing a reading indicative of concentration of a medically significant component of a body fluid.

According to the invention, a colorimeter for converting a color output to an electrical signal comprises a color chart for comparing to a color which is to be converted, means for generating an electrical signal which corresponds to a favorable comparison of the color to the color chart, and means for locating the colors of the chart with respect to the means for generating an electrical signal so that the means for generating an electrical signal is conveniently located to be actuated when the color which is to be converted approximates a color on the chart.

Illustratively according to the invention, the means for generating an electrical signal comprises a plurality of switches, each having two states, means for combining the states of the switches to provide the electrical signal which corresponds to a favorable comparison of the color to the color chart, and means for coupling the electrical switches to the means for combining the states of the switches.

Further, illustratively, the means for locating the colors of the chart with respect to the means for generating an electrical signal comprises a wheel, and means for mounting the wheel for rotation about its axis. The wheel includes two opposite generally axially facing surfaces, a first one of which includes an index and a region for receiving the color chart. The color chart includes means complementary with the index to locate the color chart with respect to the wheel. Each of the switches includes a switch actuator. The second of the two opposite, generally axially facing surfaces includes means for providing a switch actuating profile. The switches are mounted so that their actuators project close enough to the second axially facing surface to be actuated by the switch actuating profile. Rotation of the wheel thereby causes respective ones of the switches to change state.

Additionally according to an illustrative embodiment of the invention, the color to be converted comprises a serum chemistry. A strip supports the serum chemistry. The colorimeter further comprises means for holding the strip to maintain the serum chemistry in closely spaced orientation to the first axially facing surface. This facilitates comparison of the color of the serum chemistry to the colors on the color chart.

The invention may best be understood by referring to the following description and accompanying drawings which illustrate the invention. In the drawings:

FIG. 6 illustrates a top plan view of another apparatus constructed according to the invention;

FIG. 7 illustrates a top plan view of another apparatus constructed according to the invention; and FIG. 8 illustrates in partly block and partly schematic form a circuit of the apparatus of FIG. 7.

Figures 1, 2:
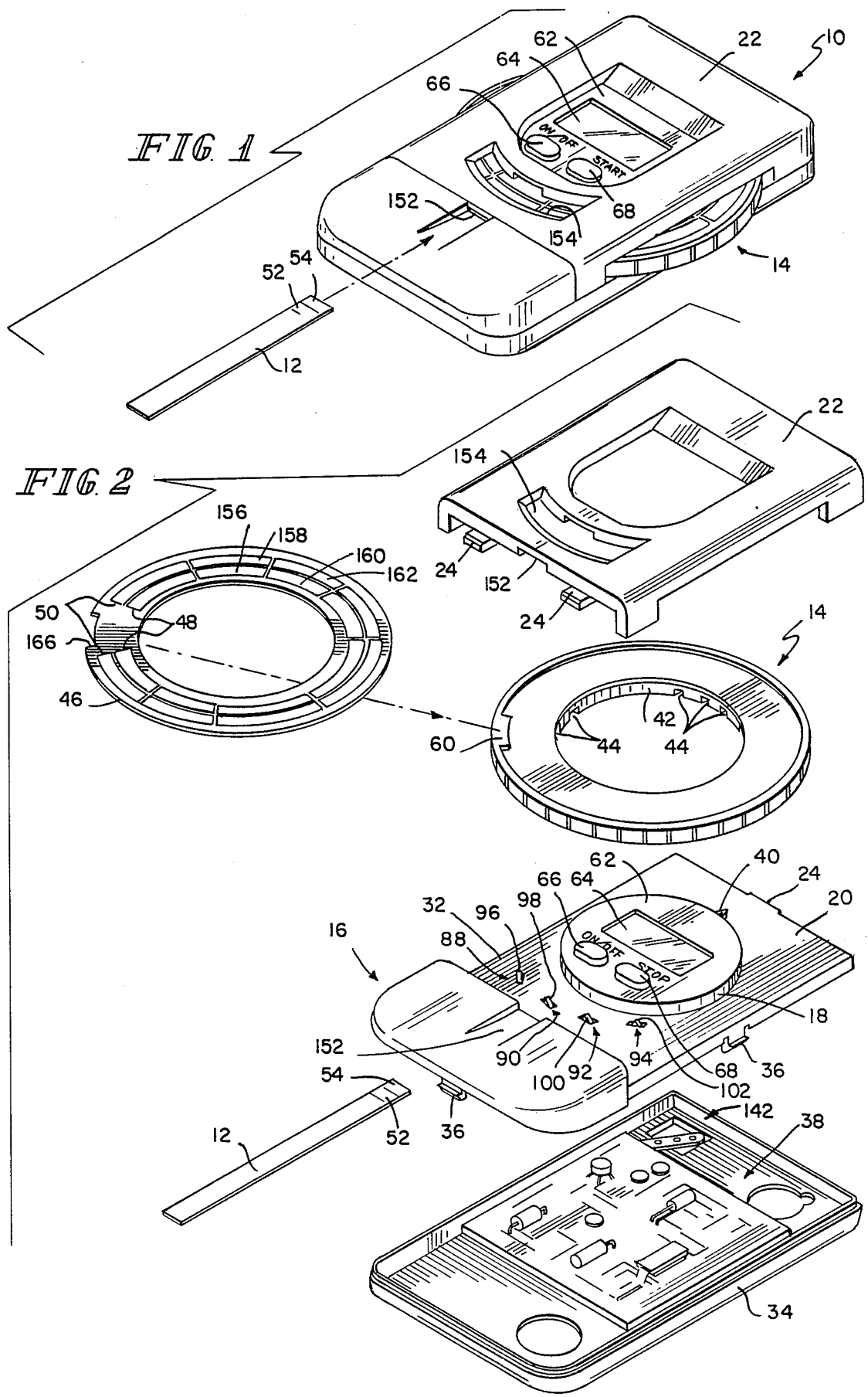
FIG. 1 illustrates a perspective view of an apparatus constructed according to the present invention.
FIG. 2 illustrates an exploded perspective view of the apparatus of FIG. 1.

Turning now to FIGS. 1-2, a colorimeter 10 for matching colors on a reacted chemical bearing strip 12 to colors on a wheel 14 includes a case 16. Case 16 includes a post 18 projecting upward from a surface 20 thereof for rotatably mounting wheel 14. A cover and retainer 22 and case 16 include projections 24 which engage in slots provided on case 16 and retainer 22 to fix retainer 22 to case 16 and thereby retain wheel 14 rotatably on post 18. Case 16 includes an upper case portion 32 and a lower case portion 34 which are joined in a snap fit by similar projections 36. Case portions 32, 34 define an interior 38 which houses the circuitry of FIG. 4, as will be explained.

Post 18 is provided with a radial spring detent 40. The radially inner circumference 42 of wheel 14 is provided with multiple, angularly spaced notches 44 for engagement by detent 40 to position wheel 14 in certain orientations. A circular, adhesive-backed color chart 46 includes two circumferentially extending adjacent rows 48, 50 of colors which correspond to the colors evolved by certain concentrations of glucose in a droplet of blood exposed for a predetermined reaction period to the juxtaposed chemistries 52, 54 on the end of strip 12. An illustrative strip 12 is the CHEMSTRIP bG ® visual test strip available from Boehringer Mannheim Diagnostics Division, 9115 Hague Road, Indianapolis, Ind., U.S.A., 46250. Wheel 14 also is provided on its upwardly facing surface 58 with a locator boss, or index, 60 which aids to position color chart 46 correctly as will be discussed.

The upwardly facing surface 62 of post 18 is provided with openings through which a liquid crystal display (LCD) 64 is visible, and an on/off button 66 and a start button 68 are accessible. LCD 64 and operating buttons 66, 68 are part of the electrical circuit of FIG. 4, and will be further described in connection with that Figure.

Figure 3:
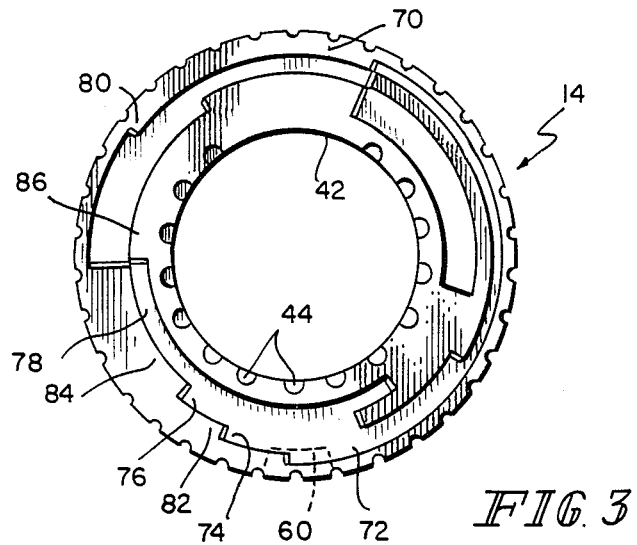
FIG. 3 illustrates a bottom plan view of a detail of the apparatus of FIGS. 1-2.

Referring to FIG. 3, the underside 70 of wheel 14 includes four circumferentially extending tracks 72, 74, 76, 78 containing boss regions 80, 82, 84, 86, respectively. Four switches 88, 90, 92, 94 are mounted in case 16 and include respective actuators 96, 98, 100, 102 which extend through respective openings in case 16 into proximity to tracks 72, 74, 76, 78, respectively. The actuators 96, 98, 100, 102 project into sufficiently closely spaced orientation with respect to tracks 72, 74, 76, 78, respectively, that the boss regions 80, 82, 84, 86 cause switches 88, 90, 92, 94, respectively, to change state when the actuators 96, 98, 100, 102 encounter their respective boss regions 80, 82, 84, 86 as wheel 14 is rotated.

Figure 4:
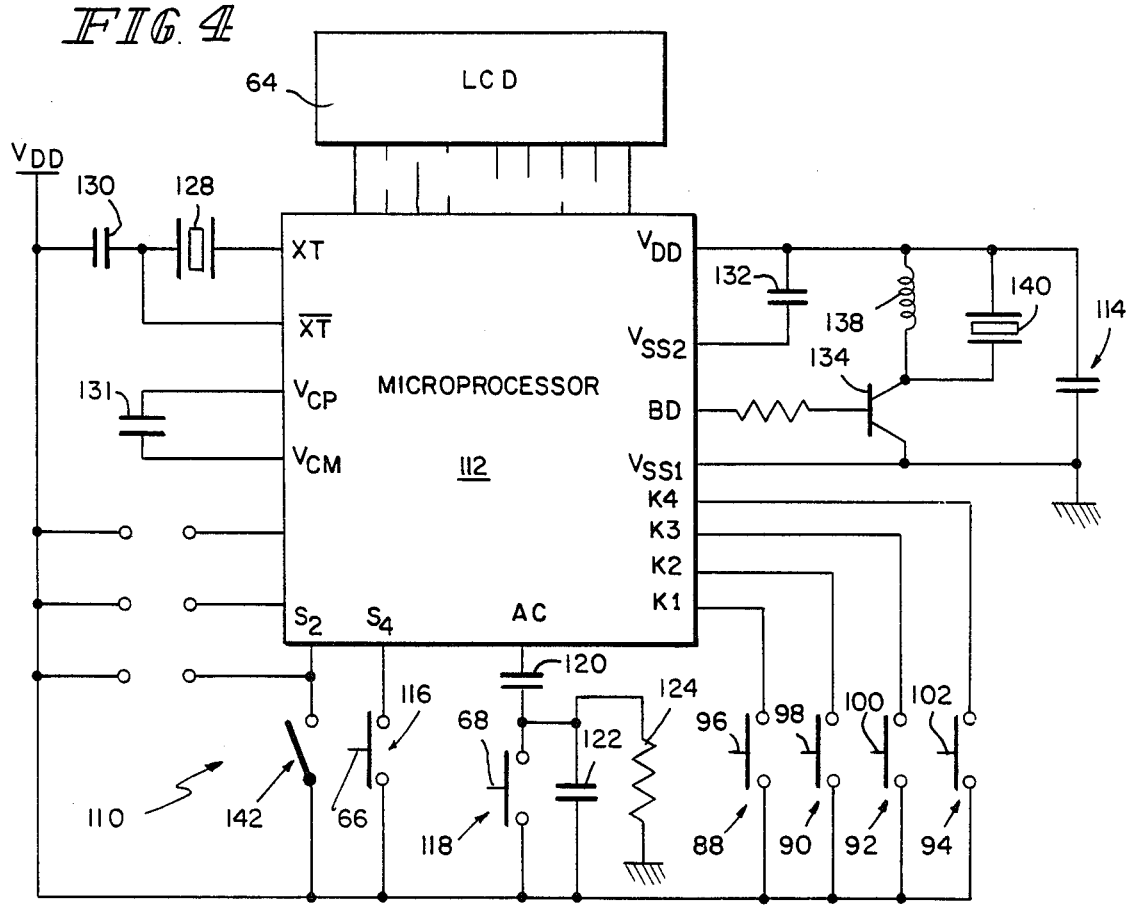
FIG. 4 illustrates in partly block and partly schematic form the circuit of the apparatus of FIGS. 1-2.
Figure 5A:
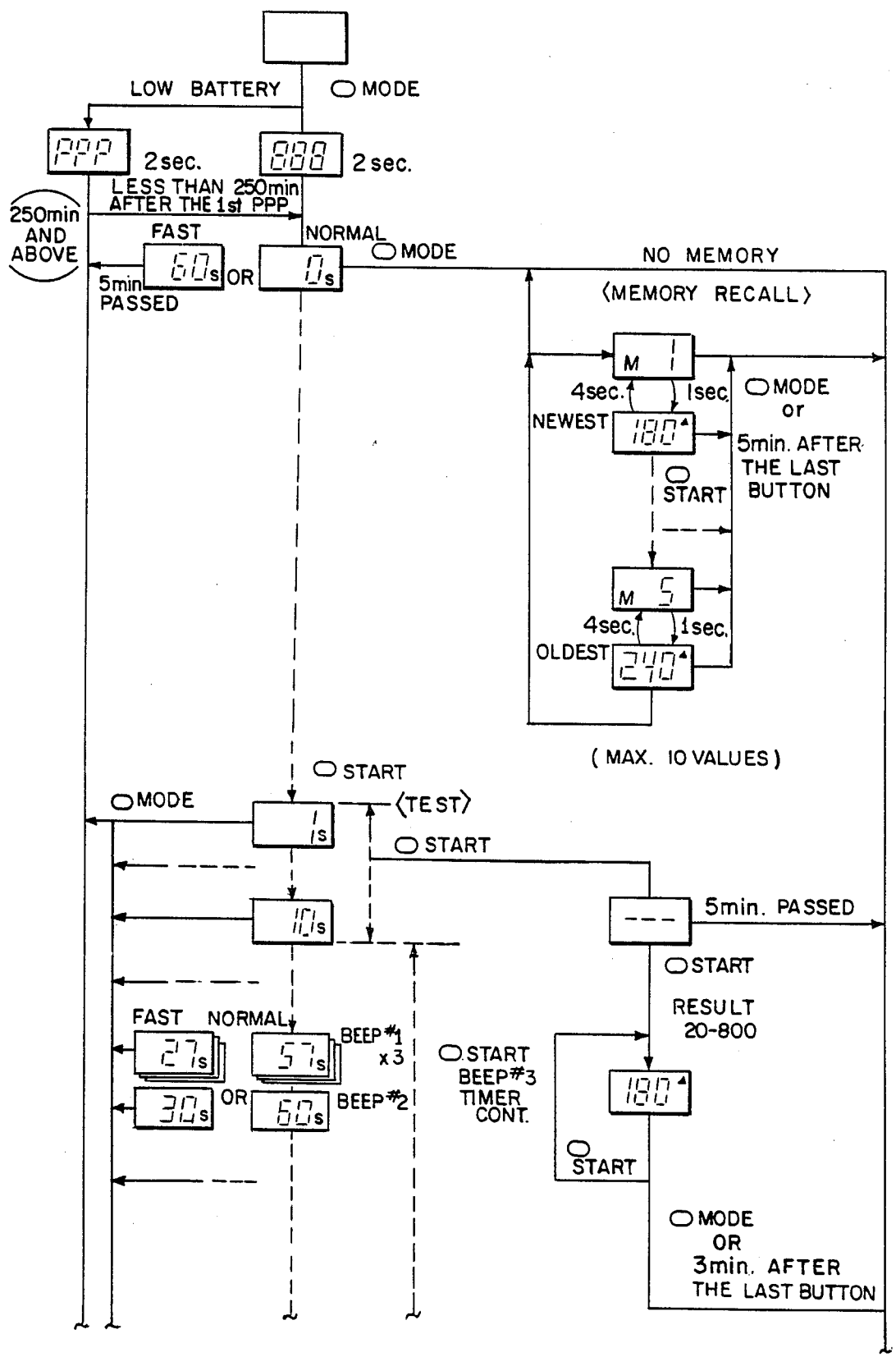
FIG. 5 illustrates a flow chart useful in understanding the operation of the apparatus of FIGS. 1-4.
Figure 5B:
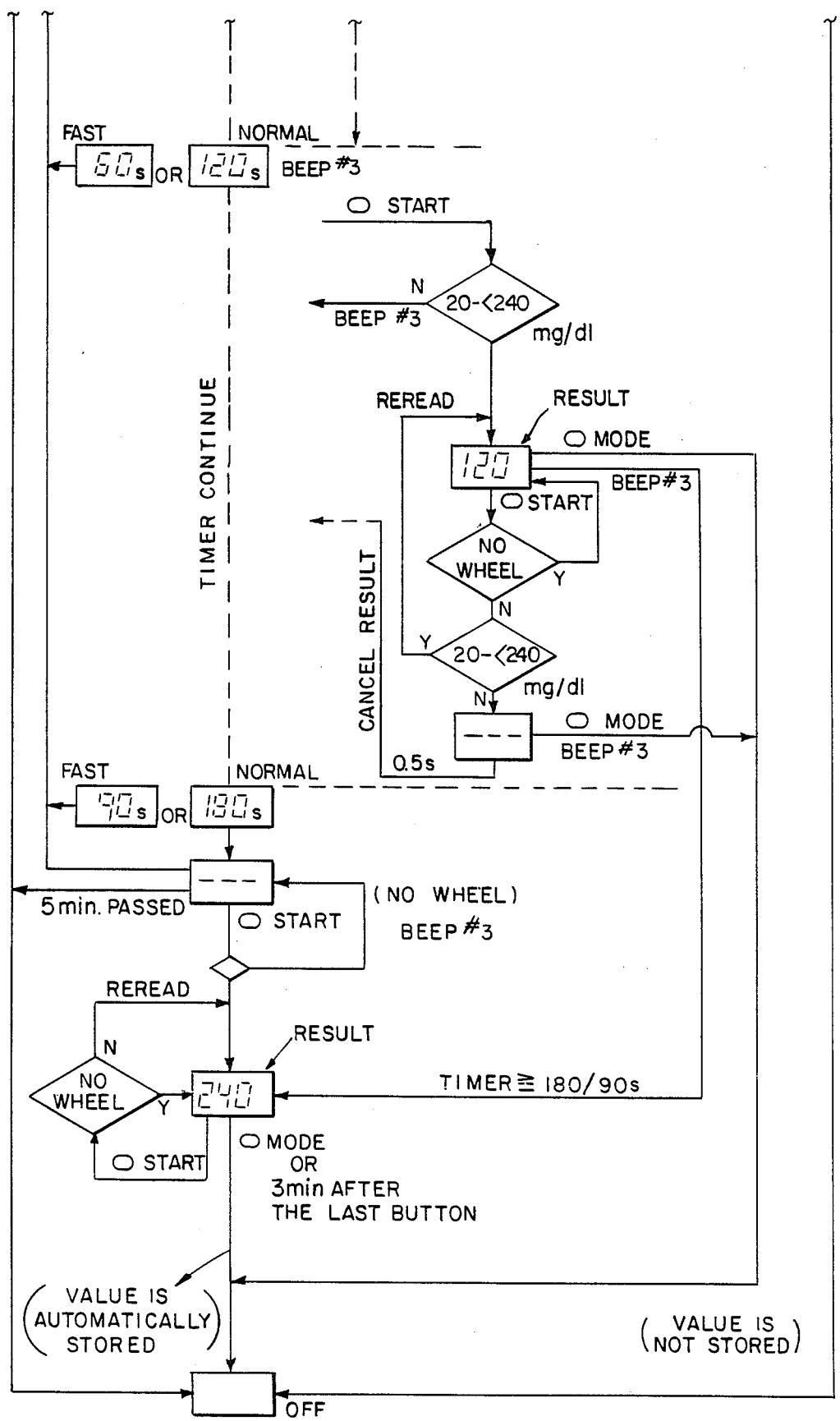

Referring now to FIG. 4, an electric circuit 110 combines the states of switches 88, 90, 92, 94 into a reading of the blood glucose concentration in, for example, the conventional units of milligrams of glucose per deciliter of blood (mg/dl). Circuit 110 includes a microprocessor ($\mu$p) 112 for combining the switch 88, 90, 92, 94 orientations into the mg/dl reading, which is then displayed on LCD 64 to which $\mu$p 112 is coupled. LCD 64 illustratively is a type LD-B 9263A LCD available from Seiko-Epson. $\mu$p 112 and its associated components are powered by a 1.55 volt watch battery 114. The + terminal of battery 114 forms the $V_{DD}$ terminal of circuit 110 and the − terminal of battery 114 forms the $V_{SS1}$ terminal of circuit 110. $\mu$p 112 illustratively is an Omron Tateisi Electronics Co. type MSN 5057 integrated circuit. The terminal names and numbers illustrated in FIG. 4 and discussed in connection with FIG. 4 are those pertinent to this integrated circuit. It is understood that no limitation is intended by this description, since other discrete or integrated circuits may be used for the purposes to which this circuit is put.

Button 66 controls a pushbutton on/off switch 116 coupled between terminals $V_{DD}$ and S4 of $\mu$p 112. Button 68 controls a pushbutton start switch 118 coupled in series with a 0.01 $\mu$F, 25 V capacitor 120 between terminals $V_{DD}$ and AC of $\mu$p 112. A 0.01 $\mu$F, 25 V capacitor 122 is coupled in parallel with switch 118, and a 100K resistor 124 is coupled between the common terminal of capacitors 120, 122 and the $V_{SS1}$ terminal. Switches 88, 90, 92, 94 are coupled between terminals $V_{DD}$ and K1, K2, K3, K4, respectively, of $\mu$p 112. A 32.768 KHz crystal 128 is coupled across terminals XT and $\overline{XT}$ of $\mu$p 112. A 22 PF, 50 V capacitor 130 is coupled across terminals XT and $V_{DD}$. A 0.1 $\mu$F, 25 V capacitor 131 is coupled between terminals $V_{CP}$ and $V_{CM}$ of $\mu$p 112. A 0.1 $\mu$F, 25 V capacitor 132 is coupled across terminals $V_{DD}$ and $V_{SS2}$ of $\mu$p 112. The base of a transistor 134, which illustratively is a type 2SD601A-R, is coupled through a 10K resistor to terminal BD of $\mu$p 112. The collector of transistor 134 is coupled through a parallel circuit including a 50 mH inductor 138 and a buzzer 140 to $V_{DD}$. Illustratively, buzzer 140 is a type KBS-15DB-4A-10 buzzer, available from Kyoto Ceramic. The emitter of transistor 134 is coupled to $V_{SS1}$. A scaling switch 142, which is only accessible from within case 16, is coupled between terminals $V_{DD}$ and S2 of $\mu$p 112.

In operation, the user actuates colorimeter 10 by pushing on/off button 66, closing switch 116. 888 appears on LCD 64 for two seconds. The user next selects a strip 12, obtains a blood sample and deposits a droplet of blood on the chemistries 52, 54 on the end of the strip. Simultaneously the user pushes start button 68 starting the timing function of $\mu$p 112. LCD 64 begins counting toward 180 seconds (90 seconds if scaling switch 142 is closed). At the display of 57, 58 and 59 seconds on LCD 64, buzzer 140 buzzes once, twice and three times, respectively. At 60 seconds, buzzer 140 buzzes once, somewhat longer. This signals the user to wipe the blood droplet from chemistries 52, 54.

When LCD 64 displays 120 seconds, a buzz of the same duration as at 60 seconds signals the user to take readings of the colors of the chemistries 52, 54. The strip 12 is inserted into the holder 152 provided therefor on case 16 until chemistries 52, 54 are visible through a window 154 through which adjacent colored sections 156, 158 and 160, 162 of chart 46 are also visible on both sides of strip 12. The user then turns wheel 14 between the stops provided by detent 40 and notches 44 until the colors of chemistries 52, 54 either match those of a colored section 156, 158 which appears on both sides of strip 12 or lie between the colors of two adjacent colored sections 156, 158 and 160, 162. There are a sufficient number of notches 40 and colored sections 156, 158, 160, 162 are long enough to permit either of these situations.

At this time, the user depresses the start button 68, causing $\mu$p 112 to read the states of switches 88, 90, 92, 94 which encode the corresponding mg/dl glucose, owing to the configurations of boss regions 80, 82, 84, 86. This result is displayed on LCD 64. If the blood glucose level is 240 mg/dl or above, the user may not be able to get a reading at 120 seconds. However, timing continues until LCD 64 displays 180 seconds, at which time buzzer 140 sounds again. This signals the user to try to take a reading again. This reading is performed in the same manner as just described. Again, the result of the reading is displayed.

The last ten readings are maintained in the memory of μp 112 and can be called up serially by pressing the on/off button 66 to turn colorimeter 10 on, and then pressing it again. The first stored value will be displayed on LCD 64. Additional stored values can be called up sequentially from memory by pushing the start button 68 one or more times.

In certain cases, the user may use "faster" chemistries, that is, ones whose reaction rates with blood glucose are more rapid. In the case of a set of chemistries whose reaction rates are approximately twice those of chemistries 52, 54, the user can open case 16 by separating case portions 32, 34 and close scaling switch 142. This speeds up the timing so that the "alert" buzzes which occurred at 57, 58 and 59 seconds in the above description now occur at 27, 28 and 29 seconds, the "wipe off blood droplet" buzz which occurred at sixty seconds now occurs at thirty seconds, the "take reading" buzz which occurred at 120 seconds now occurs at 60 seconds, and the "take reading" buzz which occurred at 180 seconds now occurs at 90 seconds.

It is also possible to read into the colorimeter 10's memory a blood glucose value corresponding to the color of a previously reacted strip. This is done by inserting the reacted strip as described above, pressing on/off button 66, start button 68, and then within ten seconds pressing start button 68 again. LCD 64 will display ---. Wheel 14 can then be dialed to the appropriate color or colors. Pressing start button 68 again will cause the blood glucose level corresponding to the dialed color or colors to be displayed on LCD 64.

The μp 112 also has a low battery warning. When battery 114 is capable of making fifty or fewer readings, LCD 64 displays PPP instead of 888 when on/off button 66 is first depressed. μp 112 also automatically turns colorimeter 10 off three minutes after a result is displayed and after five minutes if neither button 66 nor button 68 is pushed.

Because the test chemistries 52, 54 can, and typically do, vary somewhat from batch to batch, it is necessary to be able to recalibrate colorimeter 10 for each new batch of strips 12 used. This can be done by including with each package of strips 12 a color chart 46 with appropriate colors appropriately spaced from a notch 166. Notch 166 is sized to receive boss 60 to position color chart 46 correctly on wheel 14 for correct reading of the positions of bosses 80, 82, 84, 86 by actuators 96, 98, 100, 102.

Alternatively, the recalibration can be achieved by having a fixed color chart and entering a strip 12 batch-specific code. This is analogous to existing "standard curve" or "master curve" technology, such as is used in the TRACER blood glucose monitor available from Boehringer Mannheim Corporation By entering the code using one or more keys, a batch-specific interpretation of the color blocks on a fixed color chart can be established. Other coding methods would involve providing some type of optical, magnetic or electronic code carrier, such as a ROM chip, with each vial of test strips and reading this code information into the colorimeter.

In another embodiment of the invention illustrated in FIG. 6, a colorimeter 200 includes a case 206 having a generally rectangular surface 208 to which an adhesive-backed, generally rectangular color chart 236 is affixed. Color chart 236 includes adjacent rows 238, 240 of color strips for matching to the reacted chemistries 242, 244 of a strip 246. A button 248 is located next to each pair of color strips and is actuable by the user to indicate when a color match is found. Adjacent strips are close enough together that the user has little difficulty deciding which colors are closer to the colors of the chemistries 242, 244 on the reacted strip 246 and depressing the appropriate button 248 closest to those. A LCD display 252 displays the mg/dl glucose with which that button 248 is associated.

In another embodiment of the invention illustrated in FIGS. 7-8, two wheels 260, 262 are provided. Each wheel 260, 262 is provided with a respective color chart 264, 266. Each wheel 260, 262 is mounted on a respective shaft 276, 278 which controls the position of a wiper 280, 282 of a respective potentiometer 284, 286. Analog/digital converters 290, 294 transform the analog resistance values into concentration values according to a fixed correlation residing in the software of the colorimeter 200's microprocessor 296. Thus, two concentration results are obtained from matching the two chemistries that have plausibility check, a weighted average of the two results is displayed as the final test result on a digital display 292. The weight factors are pre-programmed in the software of the colorimeter 200 according to the sensitivity of the respective chemistry in the range chosen by the positions of the wheels when matching the colors.

In another, simpler embodiment of the invention, one wheel with a single color chart is provided. In this case, there is only one potentiometer as described above. The analog output, an electric current, can be measured directly with an ammeter, the scale of which is calibrated to read concentration units of the analyte, for example, mg/dl glucose. The ammeter output thus is an analog output instead of a digital output.

What is claimed is:

1. A colorimeter for converting a color output to an electrical signal comprising a color chart for comparing to a color which is to be converted, means for generating an electrical signal which corresponds to a favorable comparison of the color to the color chart, and means for locating the colors of the chart with respect to the means for generating an electrical signal so that the means for generating an electrical signal is conveniently located to be actuated when the color which is to be converted approximates a color on the chart, the means for generating an electrical signal comprising a plurality of switches, each having two states, means responsive to the states of the switches for providing the electrical signal which corresponds to a favorable comparison of the color to the color chart, and means for coupling the electrical switches to the means responsive to the states of the switches.

2. A colorimeter comprising a case, a display means mounted on said case, a color chart, means for mounting the color chart on said case to permit holding of a specimen to be compared in close proximity to the means for mounting the color chart, means for indicating which color on the color chart the color of the specimen most closely approximates, and means for coupling the indicating means to the display means to drive the display means to display an indication of the color on the color chart which most closely approximates the color of the specimen, the means for indicating which color on the color chart the color of the specimen most closely approximates comprising a plurality of switches, each having two states, each switch located adjacent a color on the color chart, and the means for coupling the indicating means to the display means comprises means for using the states of the switches to drive the display means to display a reading corresponding to the color on the color chart which most closely approximates the color of the specimen.

3. A meter for measuring the color to which a chemical test piece has turned after being contacted with a test specimen, the meter comprising a case including means for locating and holding the test piece, a color chart, means for mounting the color chart relative to the case, the chart containing colors which the chemical test piece may assume after being contacted with the test specimen, means for generating an electrical signal when the color to which the test piece has turned corresponds generally to a color on the chart, a display, and means for coupling the means for generating an electrical signal to the display to provide a meter readout related to the color to which the test piece has turned, the means for generating the electrical signal when the color to which the test piece has turned corresponds generally to a color on the chart comprising a plurality of switches, means for mounting the switches in the case adjacent the color chart, selection of a color from the color chart which corresponds generally to the color of the test piece and actuation of a switch that color causing the display to provide a meter readout related to the color to which the test piece has turned.

* * * * *

UNITED STATES PATENT AND TRADEMARK OFFICE
CERTIFICATE OF CORRECTION

PATENT NO. : 4,871,258

DATED : October 3, 1989

INVENTOR(S) : Bernd G. Herpichboehm et al.

It is certified that error appears in the above-identified patent and that said Letters Patent is hereby corrected as shown below:

At column 6, line 27, after the word "have", please insert the following --different sensitivities to the analyte. After a--.

Signed and Sealed this

Twenty-fourth Day of July, 1990

*Attest:*

HARRY F. MANBECK, JR.

*Attesting Officer*  *Commissioner of Patents and Trademarks*

UNITED STATES PATENT AND TRADEMARK OFFICE
CERTIFICATE OF CORRECTION

PATENT NO. : 4,871,258

DATED : October 3, 1989

INVENTOR(S) : Bernd G. Herpichboehm; George H. Sierra; Robert B. Summers; and Thomas M. Watlington It is certified that error appears in the above-identified patent and that said Letters Patent is hereby corrected as shown below:

In col. 8, line 14 (claim 3, line 20) after "switch" and before "that", insert --adjacent--.

Signed and Sealed this

Twenty-ninth Day of October, 1991

*Attest:*

HARRY F. MANBECK, JR.

*Attesting Officer*  *Commissioner of Patents and Trademarks*

UNITED STATES PATENT AND TRADEMARK OFFICE
CERTIFICATE OF CORRECTION

PATENT NO. : 4,871,258

DATED : October 3, 1989

INVENTOR(S) : Bernd G. Herpichboehm; George H. Sierra; Robert B. Summers; and Thomas M. Watlington It is certified that error appears in the above-identified patent and that said Letters Patent is hereby corrected as shown below:

In col. 8, line 14 (claim 3, line 20) after "switch" and before "that", insert --adjacent--.

Signed and Sealed this

Tenth Day of November, 1992

Attest:

DOUGLAS B. COMER

Attesting Officer

Acting Commissioner of Patents and Trademarks